United States Patent [19]

Lassman et al.

[11] 4,056,624

[45] Nov. 1, 1977

[54] METHOD OF TREATING DERMAL INFLAMMATION

[75] Inventors: Howard B. Lassman, Flemington; William J. Novick, Jr., Lebanon, both of N.J.

[73] Assignee: American Hoechst Corporation, Bridgewater, N.J.

[21] Appl. No.: 686,525

[22] Filed: May 14, 1976

[51] Int. Cl.² .................. A61K 31/40; A61K 31/66
[52] U.S. Cl. ................................. 424/274; 424/212
[58] Field of Search .................... 424/220, 274, 212

[56] References Cited

U.S. PATENT DOCUMENTS 3,878,225  4/1975  Allen et al. ..................... 424/274

Primary Examiner—Stanley J. Friedman
Attorney, Agent, or Firm—Curtis, Morris & Safford

[57] ABSTRACT

A method of treating dermal inflammation by topically administering to a patient an effective amount of a condensed pyrrole bearing a N-phenyl substituent and compositions containing an aforesaid pyrrole are described.

14 Claims, No Drawings

METHOD OF TREATING DERMAL INFLAMMATION

This invention relates to a novel method of treating inflammations in the dermal layers of mammals which involves the topical administration to a patient of an effective amount of a condensed pyrrole bearing an N-phenyl substituent and to compositions containing an aforesaid pyrrole.

The pyrroles disclosed herein for the treatment of dermal inflammations have been previously described and demonstrated to be systemic antiinflammatory agents by Allen et al. in U.S. Pat. No. 3,878,225 which issued Apr. 15, 1975. However, the aforesaid pyrroles have not, heretofore, been described as topical antiinflammatory agents enabling their use in the treatment of dermal inflammations. Utility as these pyrroles as described herein is surprising and unanticipated for several reasons. The skin is a unique organ; while the etiology of inflammations of the skin is not completely understood, it is generally recognized that it differs substantially from the etiology of systemic inflammations. Further, absorption of compounds through the multifold dermal layers involves quite a different set of physiochemical requirements than absorption/distribution processes on a systemic basis. For these reasons it is appreciated that it is not expected that systemically effective antiinflammatory agents are also topically effective, especially in the case of non-steroids. Further surprising is the efficacy of the topical antiinflammatory agents described herein. Their efficacy is either comparable or superior to steroids which are well recognized potent antiinflammatory agents. Additionally, it is surprising that the topical antiinflammatory agents of the present invention while exhibiting comparable or superior efficacy to the steroids do not exhibit the serious side effects which often accompany topical steroid therapy.

The method of the invention involves utilization of a pyrrole of the formula

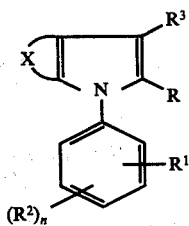

wherein R is alkyl of from 1 to 6 carbon atoms, thienyl, phenyl, diphenyl or phenyl substituted by halogen, trifluoromethyl, alkyl of from 1 to 6 carbon atoms, alkoxy of 1 to 6 carbon atoms, nitro, cyano or hydroxy; $R^1$ is carboxy, alkoxycarbonyl of from 2 to 7 carbon atoms, carbamoyl, N-alkylcarbamoyl of from 2 to 7 carbon atoms, N,N-dialkylcarbamoyl of from 3 to 7 carbon atoms, hydroxycarbamoyl or dialkylphosphinylalkoxycarbonyl of from 4 to 10 carbon atoms; $R^2$ is hydrogen, hydroxyl, mercapto, halogen, trifluoromethyl, alkoxy of from 1 to 6 carbon atoms, alkanoyloxy of from 1 to 6 carbon atoms, amino, alkanoylamino of from 1 to 6 carbon atoms, dialkylthiocarbamoyloxy of from 3 to 7 carbon atoms or dialkylcarbamoylthio of 3 to 7 carbon atoms; $R^3$ is hydrogen, alkanoyl of from 1 to 6 carbon atoms or phenyl; X is alkylene of from 3 to 5 carbon atoms, alkylene of from 3 to 5 carbon atoms substituted by alkyl or alkoxy of from 1 to 6 carbon atoms, divinylene, divinylene substituted by alkyl of from 1 to 6 carbon atoms or

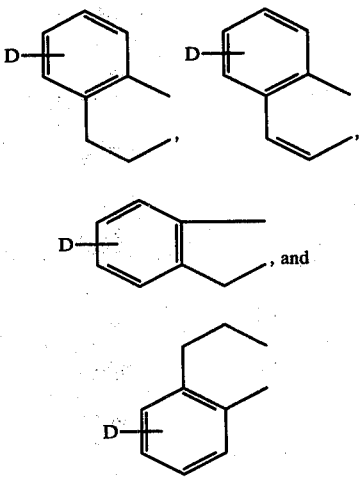

wherein D is hydrogen, alkoxy of from 1 to 6 carbon atoms or halogen; and n is the integer 1 or 2.

Pyrroles which are preferred as topically administered antiinflammatory agents are those wherein R is phenyl, $R^1$ is carboxyl and is attached to the meta position in relation to the position attached to the nitrogen atom, and $R^2$ is hydroxyl or acetoxy and is attached to the para position in relation to the position attached to the nitrogen atom, and n is 1.

The pyrroles used in the method of this invention are prepared as described in the aforesaid patent of Allen et al.

The compounds described herein are suitable as topical antiinflammatory agents due to their ability to suppress dermal inflammations in mammals. One method of assessing this ability is the croton oil induced edema assay in mice [Endocrinology, 77, 625 (1965); Clin. Pharmacol. and Therap., 16, 900 (1974)]. Accordingly, representative compounds were applied to the ear of a mouse in which said edema was induced. In was found, as shown below in Table I, that these compounds are very effective in reducing this edema. In this table the results are shown in terms of a percent decrease of edema at a mg. dose/ear.

TABLE I

| Compound | % decrease of edema | dose mg/ear |
|---|---|---|
| 3-(4-acetoxy-3-carboxyphenyl)-4,5-dihydro-2-phenylbenz[e]-indole | 50 | 0.7 |
| 1-(3-caboxy-4-hydroxyphenyl)-2-phenylindole | | |
| 1-(4-acetoxy-3-carboxyphenyl)-2-phenylindole | 50 | 0.8 |
| 1-(4-acetoxy-3-carboxyphenyl)-2-phenyl-4,5,6,7-tetrahydro-indole | 50 | 0.8 |
| 1-(3-carboxy-4-hydroxyphenyl)-2-phenyl-4,5,6,7-tetrahydro-indole | 50 | 0.9 |
| 1-(3-carboxy-4-hydroxyphenyl)-2-phenylindole | 50 | 1.8 |
| 3-(3-carboxy-4-hydroxyphenyl)-4,5-dihydro-2-phenylbenz[e]indole | 27 | 1.0 |
| | 48 | 2.5 |

To effectively utilize the topical antiinflammatory agents of this invention, said agents may be incorporated into solutions, suspensions, ointments, creams or salves that are topically administerable to the inflamed areas of patients. These preparations should contain at least 0.01% of the active compound, more desirably between about 0.05 and about 20% by weight. The amount of active compound in such compositions is such that a suitable dosage will be obtained. Preferred compositions for the treatment of dermal inflammations are those containing between 0.1 and 10% of the active compound.

The topical compositions may also include the following components: water, fixed oils, polyethylene glycols, glycerol, petroleum, stearic acid, beeswax, other synthetic solvents or mixture thereof; antibacterial agents such as benzyl alcohol or methyl paraben; antioxidants such as α-tocopherol acetate; chelating agents such as ethylenediaminetetracetic acid; buffers such as acetates, citrates or phosphate; emulsifying agents such as polyoxyethylene monooleate and coloring materials and adjuvants such as ferric oxide or talc. The topical preparations can be enclosed in tubes, bottles or jars made of metal, glass or plastic.

We claim:

1. A method of treating inflammation in the dermal layers of mammals which comprises topically administering to the inflamed area of a patient an effective amount of a pyrrole of the formula

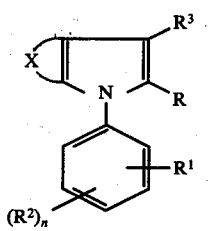

wherein R is alkyl of from 1 to 6 carbon atoms, thienyl, phenyl, diphenyl or phenyl substituted by halogen, trifluoromethyl, alkyl of from 1 to 6 carbon atoms, alkoxy of 1 to 6 carbon atoms, nitro, cyano or hydroxy; $R^1$ is carboxy, alkoxycarbonyl of from 2 to 7 carbon atoms, carbamoyl, N-alkylcarbamoyl of from 2 to 7 carbon atoms, N,N-dialkylcarbamoyl of from 3 to 7 carbon atoms, hydroxycarbamoyl or dialkylphosphinylalkoxycarbonyl of from 4 to 10 carbon atoms; $R^2$ is hydrogen, hydroxyl, mercapto, halogen, trifluoromethyl, alkoxy of from 1 to 6 carbon atoms, alkanoyloxy of from 1 to 6 carbon atoms, amino, alkanoylamino of from 1 to 6 carbon atoms, dialkylthiocarbamoyloxy of from 3 to 7 carbon atoms or dialkylcarbamoylthio of 3 to 7 carbon atoms; $R^3$ is hydrogen, alkanoyl of from 1 to 6 carbon atoms or phenyl; X is alkylene of from 3 to 5 carbon atoms, alkylene of from 3 to 5 carbon atoms substituted by alkyl or alkoxy of from 1 to 6 carbon atoms, divinylene, divinylene substituted by alkyl of from 1 to 6 carbon atoms or

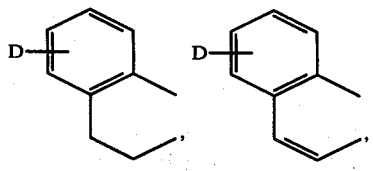

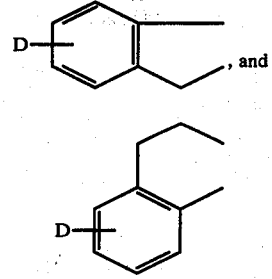

wherein D is hydrogen, alkoxy of from 1 to 6 carbon atoms or halogen; and n is the integer 1 or 2.

2. The method as defined by claim 1 wherein R is phenyl.

3. The method as defined by claim 1 wherein R is tertiary butyl, thienyl, phenyl, diphenyl or phenyl substituted by chlorine, bromine, fluorine, hydroxyl, trifluoromethyl, methyl, methoxy, nitro or cyano; $R^1$ is carboxyl, methoxycarbonyl, ethoxycarbonyl, carbamoyl, N-ethylcarbamoyl, N,N-diethylcarbamoyl, hydroxycarbamoyl or dimethylphosphinylmethoxycarbonyl; $R^2$ is hydrogen, hydroxyl, mercapto, chlorine, bromine, trifluoromethyl, methoxy, acetoxy, acetylamino, dimethylthiocarbamoyloxy or dimethylcarbamoylthio; $R^3$ is hydrogen, acetyl or phenyl; and X is alkylene of from 3 to 5 carbon atoms, butylene substituted by methyl, tertiary butyl or methoxy, divinylene, divinylene substituted by tertiary butyl or

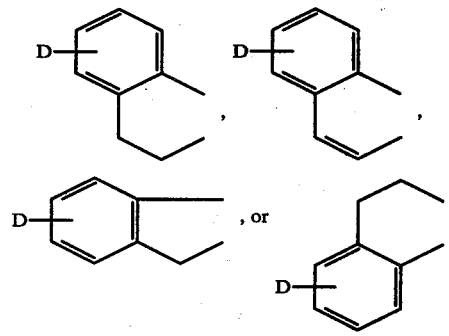

wherein D is hydrogen, methoxy or chlorine.

4. The method as defined by claim 3 wherein R is phenyl.

5. A method of treating inflammation in the dermal layers of mammals which comprises topically administering to the inflamed area of a patient an effective amount of a pyrrole of the formula

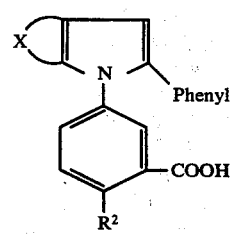

wherein $R^2$ is hydroxyl or alkanoyloxy of from 1 to 6 carbon atoms; X is alkylene of from 3 to 5 carbon atoms, divinylene,

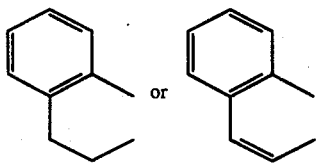 or

6. The method as defined by claim 5 wherein $R^2$ is hydroxyl.

7. The method as defined by claim 5 wherein $R^2$ is acetoxy.

8. The method as defined by claim 5 in which 3-(4-acetoxy-3-carboxyphenyl)-4,5-dihydro-2-phenylbenz[e]indole is administered.

9. The method as defined by claim 5 in which 1-(3-carboxy-4-hydroxyphenyl)-2-phenylindole is administered.

10. The method as definded by claim 5 in which 1-(4-acetoxy-3-carboxyphenyl)-2-phenylindole is administered.

11. The method as defined by claim 5 in which 1-(4-acetoxy-3-carboxyphenyl)-2-phenyl-4,5,6,7-tetrahydroindole is administered.

12. The method as defined by claim 5 in which 1-(3-carboxy-4-hydroxyphenyl)-2-phenyl-4,5,6,7-tetrahydroindole is administered.

13. The method as defined by claim 5 in which 3-(3carboxy-4hydroxyphenyl)-4,5-dihydro-2-phenylbenz[e]indole is administered.

14. The method as defined by claim 5 in which 3-(3-carboxy-4-hydroxyphenyl)-2-phenylbenz[e]indole is administered.

* * * * *